United States Patent [19]

Burkhardt

[11] Patent Number: 5,463,131
[45] Date of Patent: Oct. 31, 1995

[54] SYNTHESIS OF ORGANOHALOBORANES AND ALKOXYORGANOBORANES

[75] Inventor: Elizabeth R. Burkhardt, Bridgeville, Pa.

[73] Assignee: Mine Safety Appliances Company, Pittsburgh, Pa.

[21] Appl. No.: 268,304

[22] Filed: Jun. 30, 1994

[51] Int. Cl.$^6$ .................................................... C07F 5/02
[52] U.S. Cl. ............................................. 568/1; 568/6
[58] Field of Search ............................................ 568/1, 6

[56] References Cited

U.S. PATENT DOCUMENTS

| | | | |
|---|---|---|---|
| 3,026,329 | of/0000 | Brown | 568/1 |
| 4,772,752 | 9/1988 | Brown | 568/1 |
| 5,043,479 | 8/1991 | Brown | 568/1 |

OTHER PUBLICATIONS

H. C. Brown, S. U. Kulkarni, J. Organomet Chem. 1982, 239, 23–41.
H. C. Brown, P. A. Tierney, J. Adm Chem. Soc. 1958, 80, 1552.
H. Noth, H. Beyer, Ber. 1950, 93, 225.
D. Pasto and P. Balasubramaniyan, J. Am. Chem. Soc. 1967, 89, 295.
D. J. Pasto and S. Kang, J. Am. Chem. Soc. 1968, 90, 3797.
K. Kinberger and W. Siebert, Z. naturforsch., B 1975, 30, 55.
H. C. Brown and N. Ravindran, J. Org. Chem. 1977, 42, 2533.
H. C. Brown and N. Ravindran, Inorg. Chem. 1977, 16, 2938.
J. Cueilleron, J. Bonix, Bull. Soc. Chim., France 1967, 2945.
H. C. Brown and P.K.Jadhav, J. Am. Chem. Soc. 1983, 105, 2092.
G. Bir, D. Kaufmann, Tetra. Letters 1987, 28, 777.
A. O. King et al., J. Org. Chem. 1993, 58, 3731–3735.
A. S. Thompson, J. Org. Chem. 1992, 57, 7044–7052.
D. S. Matteson et al., Organometallics 1984, 7, 1284–1288.
H. C. Brown et al., Organometallics, 1983, 2, 1311–1316.
H. C. Brown and S. M. Singh, Organometallics 1986, 5, 999–997.
H. C. Brown et al., Organometallics 1982, 1, 212–214.
Brown et al., J.A.C.S., vol. 98, #7, pp. 1785–1797 (1976).
Brown et al. J.A.C.S., vol. 98, #7, pp. 1798–1806 (1976).

*Primary Examiner*—James H. Reamer
*Attorney, Agent, or Firm*—Henry E. Bartony, Jr.; James G. Uber

[57] ABSTRACT

A one-step process is provided for the synthesis of organohaloboranes, including diisopinocampheylchloroborane, and alkoxyorganoboranes. The present process does not utilize a thermally unstable ether adduct or a malodorous dimethyl sulfide adduct as required in prior processes. In general, the organohaloboranes are synthesized in a single reactor by reacting olefin(s) and/or alkyne(s) with boron trihalide and diborane. Alkoxyorganoboranes are synthesized in a single reactor by reacting olefin(s) and/or alkyne(s) with alkylborate and diborane.

17 Claims, No Drawings

SYNTHESIS OF ORGANOHALOBORANES AND ALKOXYORGANOBORANES

FIELD OF THE INVENTION

The present invention relates to a novel process for the synthesis of organohaloboranes and alkoxyorganoboranes, and especially to the synthesis of diorganomonohaloboranes and organodihaloboranes.

BACKGROUND OF THE INVENTION

Chloroborane complexes, the precursors to organohaloboranes, have been prepared by a variety of methods. See H. C. Brown, S. U. Kulkarni, *J. Organomet. Chem.* 1982, 239, 23–41. For example, lithium or sodium borohydride and boron trichloride give chloroborane-ether adduct according to the following reaction:

$$MBH_4 + BCl_3 \xrightarrow{ether} 2 H_2BCl.Et_2O + MCl$$

where M=Na, Li. See H. C. Brown, P. A. Tierney, *J. Am. Chem. Soc.* 1958, 80, 1552; H. Noth, H. Beyer, Ber. 1960, 93, 225; U.S. Pat. No. 3,026,329.

A mixture of borane-tetrahydrofuran adduct and boron trichloride form chloroborane-tetrahydrofuran adduct according to the following reaction:

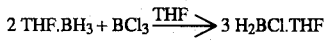

$$2 THF.BH_3 + BCl_3 \xrightarrow{THF} 3 H_2BCl.THF$$

See D. J. Pasto and P. Balasubramaniyan, *J. Am. Chem. Soc.* 1967, 89, 295; D. J. Pasto and S. Kang, *J. Am. Chem. Soc.* 1968, 90, 3797.

Borane-dimethylsulfide adduct (DMSB) and dimethylsulfide boron trichloride give dimethylsulfide chloroborane according to the following reaction:

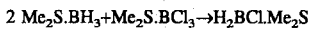

$$2 Me_2S.BH_3 + Me_2S.BCl_3 \rightarrow H_2BCl.Me_2S$$

See K. Kinberger and W. Siebert, *Z. Naturforsch.*, B 1975, 30, 55; H. C. Brown and D. Ravindran, *J. Org. Chem.* 1977, 42, 2533; H. C. Brown, *Inorg. Chem.* 1977, 16, 2938. These chloroborane ether and sulfide adducts have been used in hydroboration reactions as described in detail below.

Finally, gas phase reaction of diborane and boron trichloride gives dichloroborane according to the following reactions:

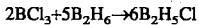

$$B_2H_6 + 4BCl_3 \rightarrow 6BCl_2$$

$$2BCl_3 + 5B_2H_6 \rightarrow 6B_2H_5Cl$$

See J. Cueilleron, J. Bonix, *Bull. Soc. Chim.*, France 1967, 2945. Although these gas phase reactions were not conducted for subsequent hydroboration reactions, they demonstrate that chloroboranes can be prepared in the absence of coordinating ether or sulfide ligands.

Diisopinocampheylchloroborane (hereafter referred to as DPC) is a very useful chiral reducing agent for prochiral ketones and imines. DPC can be prepared from α-pinene and chloroborane diethyl etherate. H. C.Brown, P. K. Jadhav. *J. Am. Chem. Soc.* 1983, 105, 2092. A variation of this process using dimethyl sulfide chloroborane has been elaborated by G. Bir and A. O. King. G. Bir, D. Kaufmann, *Tetr. Letters* 1987, 28, 777; and A. O. King et al., *J. Org. Chem.* 1993, 58, 3731–3735.

Brown purports to obtain high optical purity DPC through a two-step procedure. See U.S. Pat. Nos. 4,772,752 and 5,043,479. In this procedure, diisopinocampheylborane, a moisture and thermally sensitive intermediate is isolated from the reaction of α-pinene and DMSB. Subsequent addition of hydrogen chloride gives the final product, DPC, as a moisture sensitive solid, which is isolated from the solution. On an industrial scale this complicated process presents several technical difficulties including the handling of thermally-sensitive solids as well as the handling of moisture sensitive product.

A. S. Thompson, in *J. Org. Chem.* 1992, 57, 7044–7052, and A. O. King, supra, have shown that solutions of DPC made from >70% ee α-pinene and DMSB or dimethyl sulfide chloroborane can be used in excess to achieve high optical purity reduction products, without the need for the handling of the moisture sensitive DPC solid.

All of these processes for making DPC involve use of chloroborane-diethyl ether adduct, which is thermally unstable, or dimethyl sulfide chloroborane adduct, which is notoriously malodorous. Some of the ether and sulfide ligands cause problems in the formation and use of the organochloroboranes. For example, diorganochloroborane formed from a haloborane-tetrahydrofuran adduct can cleave tetrahydrofuran rendering the borane compound unusable. Furthermore, the sulfide adducts leave a sulfur smell on the final product. Development of a method for hydroboration of α-pinene by chloroborane to form DPC without the use of ether chloroborane adduct or sulfide chloroborane adduct is, therefore, very desirable.

SUMMARY OF THE INVENTION

Accordingly, the present invention provides a process for the generation of diorganohaloboranes and organodihaloboranes without the use of ether chloroborane adduct or sulfide chloroborane adduct. Diorganohaloboranes are useful precursors to borinic acids and esters by methods known in the art. See D. S. Matteson et al., *Organometallics* 1984, 7, 1284–1288; H. C. Brown ibid. 1983, 2, 1311–1316; ibid. 1986, 5, 994–997. Organodihaloboranes are precursors to boronic acids and esters See H. C. Brown, *Organometallics* 1982, 1,212.

Generally, the present invention provides a novel process for the preparation of organohaloboranes of the formula, $R^2R^3BX$ (a diorganohaloborane) and $RBX_2$ (an organodihaloborane), comprising the step of reacting in a single reactor an olefin(s) and/or alkyne(s) with boron trihalide and diborane according to the following general reactions:

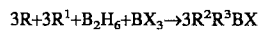
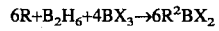

$$3R + 3R^1 + B_2H_6 + BX_3 \rightarrow 3R^2R^3BX$$

$$6R + B_2H_6 + 4BX_3 \rightarrow 6R^2BX_2$$

wherein X is a fluoro, a chloro, a bromo, or an iodo group, R is an olefin or an alkyne and $R^1$ is an olefin or an alkyne. $R^1$ can be the same as or different from R. In the above reactions, if R is an olefin, $R^2$ is the corresponding alkyl group. If R is an alkyne, $R^2$ is the corresponding alkenyl group. Likewise, if $R^1$ is an olefin, $R^3$ is the corresponding alkyl group. If $R^1$ is an alkyne, $R^3$ is the corresponding alkenyl group. In the case of $R^2R^3BX$, $R^2$ and $R^3$ can be linked together to form a ring or bicyclic system, such as B-chloro-9-borabicyclo[3.3.1]nonane. The reaction can be run neat or in any solvent compatible with the reagents and product. Examples of suitable solvents for a number of reactions under the present invention include the following hydrocarbon solvents: pentane, hexane, heptane, cyclohexane, methylcyclohexane toluene or benzene.

Moreover, alkoxydiorganoboranes and dialkoxyorganoboranes can be prepared under the above general reactions wherein X is an alkoxy group. In the synthesis of such alkoxyorganoboranes, a dialkylborane (or tetraalkyldiborane) may be added to the reaction mixture as a catalyst.

Olefins for use in the above reactions have the general formula:

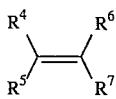

wherein $R^4$, $R^5$, $R^6$ and $R^7$ are any combination of hydrogen, an aryl group, an aralkyl, a branched alkyl group, an unbranched alkyl group or a cyclic group, such groups containing from one to ten carbon atoms. Alternatively, $R^4$ and $R^5$ can be linked by a $C_n$ chain wherein n=2–10 or $R^4$ and $R^6$ are linked by a $C_n$ chain wherein n=2–10. The aryl and alkyl groups may comprise functionalities such as ester groups, ether groups, halo groups, silyl groups or nitro groups. The olefin group may also be a terpene from a naturally derived source.

Alkynes for use in the present reaction have the general formula:

wherein $R^8$ and $R^9$ are any combination of hydrogen, an aryl group, an aralkyl group, a branched alkyl group, an unbranched alkyl group or a cyclic group, such groups containing from one to ten carbon atoms. Alternatively, $R^8$ and $R^9$ can be linked by a $C_n$ chain where n=8–15. The aryl and alkyl groups may comprise functionalities such as ester groups, ether groups, halo groups, silyl groups or nitro groups.

The present single reactor or "one-pot" process eliminates the need for coordinating ligands such as ethers or sulfides. The process generates substantially no waste by-products and can easily be run on a large scale.

Particularly useful compounds for preparation using the present process are DPC, diisocampheylchloroborane and dicyclohexylchloroborane. Dicyclohexylchloroborane is useful for the preparation of boron enolates.

DETAILED DESCRIPTION OF THE INVENTION

As used in connection with the present invention, the term "alkyl" means a branched, an unbranched, or a cyclic saturated hydrocarbon group containing one to twenty carbon atoms; the term "aralkyl" means an ω-aryl-alkyl group, wherein the aryl group may be a phenyl group, a substituted phenyl group or any other aromatic ring system; the terms "halo" or "halide" mean a fluoro, a chloro, a bromo, or an iodo group; the term "alkyne" means a compound containing a carbon-carbon triple bond; the term "olefin" means a compound containing a carbon-carbon double bond; "enantiomeric excess" (or e.e.), is defined as the excess of one of a pair of enantiomers, usually expressed as a percentage derived from the formula: [(R-S)/(R+S)]×100; the term "prochiral" describes an $sp^2$ hybridized atom which upon conversion to $sp^3$ hybridization yields a chiral center at that atom.

Preparation of Diorganohaloboranes and Alkoxydiomanoboranes

Under the present invention diorganohaloboranes are synthesized by reacting an olefin and/or alkyne (neat or in a suitable solvent) with boron trihalide and diborane. In this reaction, the mole ratio of olefin/alkyne to boron trihalide is in the range of approximately 4:1 to 10:1 and preferably in the range of approximately 6:1 and 9:1. The ratio of boron trihalide to diborane is in the range of approximately 1:1.5 and 1.5:1 and preferably in the range of approximately 1:1 and 1:1.5. The resulting reaction mixture is agitated at a temperature between about −20° C. and the reflux temperature of the system, preferably between ambient temperature and the reflux temperature of the system under an inert atmosphere (e.g., nitrogen, argon, etc.) at ambient or moderately superambient pressure, e.g. 1 to 10 bar, until the reaction is complete, typically for a time between 1 and 72 hours. The reflux temperature of the system is generally the boiling point of the solvent at the pressure of the reaction. The resulting diorganohaloborane may be used "as is" in solution or isolated from the solvent. For example, DPC can be crystallized and isolated as a solid with enhanced optical purity. Certain diorganohaloboranes may precipitate from the hydrocarbon solvent and can be easily filtered.

Alkoxydiorganoboranes can be prepared under the above synthetic scheme by substituting an alkyl borate of the general formula $B(OR^{10})_3$, wherein $R^{10}$ is an alkyl group, for the boron trihalide reactant. Preferably, $R^{10}$ is a methyl, an ethyl or an isopropyl group.

Preparation of Oroanodihaloboranes and Dialkoxyorganoboranes

Likewise, organodihaloboranes are synthesized under the present invention by reacting an olefin or alkyne (neat or in a suitable solvent) with boron trihalide and diborane. The mole ratio of olefin or alkyne to boron trihalide is typically in the range of approximately 1:1 and 2:1 and preferably 3:2. The ratio of boron trihalide to diborane is in the range of approximately 3:1 and 5:1 and preferably 4:1. The resulting reaction mixture is agitated at a temperature between about −20° C. and the reflux temperature of the system, preferably between ambient temperature and the reflux temperature of the system under an inert atmosphere (e.g. nitrogen, argon, etc.) at ambient or moderately superambient pressure, e.g. 1 to 10 bar, until the reaction is complete, typically for a time between 1 and 72 hours. The reflux temperature of the system is generally the boiling point of the solvent at the pressure of the reaction. The resulting organodihaloborane may be used as a solution or isolated from the solvent.

Dialkoxyorganoboranes can be prepared under the above synthetic scheme by substituting an alkyl borate of the general formula $B(OR^{10})_3$, wherein $R^{10}$ is an alkyl group, for the boron trihalide reactant. Preferably, $R^{10}$ is a methyl, an ethyl or an isopropyl group.

EXAMPLES

General Procedures

All experiments were conducted under nitrogen in glass or stainless steel pressure vessels equipped with either magnetic or mechanical stirring. The pressure vessels were equipped with back-pressure regulators set to release excess pressure to a methanol or aqueous NaOH scrubber.

$^1$H NMR spectra were recorded in deuterochloroform on a Bruker-250 NMR spectrometer and reported in ppm relative to an internal standard of tetramethylsilane (as 0.0 ppm). $^{11}$B NMR spectra were taken of reaction solutions or in an appropriate non-reactive solvent on a Bruker-250 NMR spectrometer at 80.25 MHz and reported in ppm relative to $BF_3.Et_2O$ (0.0 ppm) external standard. Specific rotations were determined on a JASCO DIP-370 with sodium lamp at the D line, 589 nm. Concentrations (c) for specific rotations are reported in units of g/100 mL.

Analytical gas chromatography (GC) was carried out on a Hewlett-Packard 5890A gas chromatograph with split-mode injector, flame-ionization detector and helium as the carrier gas. A chiral capillary column (30 m×0.20 mm), Cyclodex-B (J & W Associates), was used to determine optical and chemical purity of α-pinene and oxidation products of DPC.

As necessary, solvents were dried over 4A molecular sieves. Residual water content was determined by Karl Fisher titration. (+)-α-Pinene (Aldrich) was 87% ee as determined by optical rotation and chiral GC. (−)-α-Pinene (Glidco) was 80% ee.

The following examples illustrate the present invention without limitation of the same. The compounds prepared in the examples gave satisfactory boron and chloride analyses.

Example 1

(−)α-Pinene (958 g. 7.03 mol) (i.e., R=R$^1$=(−)α-Pinene) and hexane (198.4 g) were loaded into a dry nitrogen-filled, stainless steel pressure reactor. Boron trichloride (118 g. 1.01 mol) was added to the α-pinene/hexane solution. A back-pressure relief valve was set at 2 bar. The mixture was stirred while diborane (31 g, 1.1 mol) was added over 150 min. No temperature increase was observed. The solution was heated to 55°–60° C. for 5 h, then allowed to stand at ambient temperature until conversion was completed. The solution was monitored by $^{11}$B NMR to determine reaction progress. Yield: 1305 g (76.8 wt % (+) DPC in hexane) (i.e., $R^2=R^3$=isopinocampheyl group). $^1$H NMR (CDCl$_3$). 1.0–1.3 (m, 4H), 1.04 (d, 6H), 1.05 (s, 6H), 1.19 (s, 6H), 1.64–2.07 (m, 8H), 2.29 (m, 2H), 2.50 (m, 2H). $^{11}$B NMR (hexane) δ76. Boron Analysis of the Solution: 76.8 wt %. Optical Purity Analysis by Chiral GC: 84% ee.

Example 2

(−)-o,ac-pinene (1,458 g, 10.70 mol) and toluene (184 g) was loaded into a 1 gallon stainless steel pressure vessel. Boron trichloride (179.5 g, 1.532 mol) was added, followed by diborane (50 g, 1.8 mol). The reaction mixture was then heated to 60° C. for 4 h. The reaction was shown to be complete by $^{11}$B NMR after 4h. After cooling to ambient temperature, the reaction mixture was transferred to glass bottles. Yield: 1,759 g of 83 wt % (+)-DPC in toluene.

$^{11}$B NMR (Toluene) δ74 Boron Analysis of the Solution: 83 wt % Density: 0.962 g/mL at 20° C. Optical Purity Analysis by Chiral GC of Oxidized Product: 88.6% ee (+) DPC Example 3

Cyclohexene (173.5 g, 2.112 mol) and 100 ml of hexane were loaded into a dry nitrogen-filled glass pressure reactor. Boron trichloride (38 g, 0.33 mol) was added to the cyclohexene/hexane mixture. A back-pressure relief valve was set at 3.1 bar. The mixture was stirred while diborane (9 g, 0.3 mol) was added over 80 min. No temperature increase was observed. The solution was heated to 55–60° C. for 10.5 h, until conversion was complete. The $^{11}$B NMR spectrum showed 93.5% dicyclohexylchloroborane. $^{11}$B NMR (hexane) δ76.5.

Example 4

1-Hexene (224 g, 2.66 mol) and 100 mL of hexane were loaded into a dry nitrogen-filled glass pressure reactor. Boron trichloride (44 g, 0.38 mol) was added to the 1-hexene/hexane mixture. A back-pressure relief valve was set at 3.1 bar. The mixture was stirred while diborane (12 g, 0.43 mol) was added over 60 min. The solution was heated to 84° C. for 24.5 h until conversion was complete. The $^{11}$B NMR spectrum showed 95% dihexyl chloroborane. $^{11}$B NMR (hexane) δ78.

Example 5

Boron trichloride (14.6 g, 0.125 mol) was added to 100 mL of hexane in a dry nitrogen-filled glass pressure reactor. 1-Hexyne (68.5 g, 0.834 mol) and 100 mL of hexane were added to the BCl$_3$. The mixture was stirred while diborane (3.5 g, 0.13 mol) was added over 30 min. The solution was heated to 60° C. and maintained for 4.5 h until 95% conversion to dihexenylchloroborane. $^{11}$B NMR (hexane) δ73.

Example 6

Boron trichloride (14.7 g, 0.127 mol) was added to 200 mL of hexane in a dry nitrogen-filled glass pressure reactor. 1,5-Cyclooctadiene (48.1 g, 0.445 mol) was added to the BCl$_3$ solution. The mixture was stirred while diborane (4.0 g, 0.14 mol) was added over 20 min. The solution was heated for 10 h at a temperature between 65°–85° C. $^{11}$Boron NMR analysis showed 93% conversion to B-chloro-9-borabicyclo[3.3.1]nonane. $^{11}$B NMR (hexane), δ82.

Example 7

(+)-α-pinene (100.0 g, 0.734 mol) and hexane (200 ml) were loaded into a dry nitrogen-filled, glass pressure reactor. Boron trichloride (55.3 g, 0.472 mol) was added, followed by diborane (4.0 g, 0.14 mol). The reaction mixture was then heated to 40° to 60° C. for 4 days. $^{11}$Boron NMR spectra of the reaction mixture showed 91% isopinocampheyldichloroborane at δ63.

Example 8

Cyclohexene (61.2 g, 0.745 mol) and hexane (200 ml) were loaded into a nitrogen-filled glass pressure reactor. Boron trichloride (59.9 g, 0.511 mol) was added. The back-pressure regulator was set to 2 bar. Diborane (50 g, 0.18 mol) was added. The reaction mixture was heated to 50°–60° C. for 5 days. The reaction was monitored by $^{11}$Boron NMR and shown to contain 86% cyclohexyl dichloroborane δ3 64.

Example 9

(+)-α-pinene (271 g, 1.98 mol) and hexane (100 ml) were loaded into a dry nitrogen-filled, glass pressure reactor. Methyl borate (29.0 g, 0.28 mol) was loaded to the α-pinene/hexane solution. A back-pressure relief valve was set at 2 bar. The mixture was stirred while diborane (7.8 g, 0.28 mol) was added over 30 minutes. The reaction was exothermic during the diborane addition. The reaction mixture was then heated to 40° C. for 5 hours. $^{11}$Boron NMR analysis of the product showed 96% conversion to (−)diisopinocampheylmethoxyborane, 2% (−)isopinocampheyldimethoxyborane and 2% unreacted methylborate. $^{11}$Boron NMR (hexane) δ53. Boron analysis of the solution: 76%.

Example 10

Tetraethyldiborane (62.5 g, 0.447 mol) was loaded into the glass pressure vessel as a catalyst. The back-pressure regulator was set to 2 bar. Diborane (5.0 g, 0.149 mol) was added followed by methylborate (62.0 g, 0.596 mol) Ethylene (50 g, 1.8 mol) was bubbled into the solution over 4.5 hours. The reaction was exothermic and was kept between 20°–35° C. with a refrigerated bath. When ethylene uptake ceased the reaction mixture contained 61% methoxydiethylborane, 27% trimethylborane and 10% dimethoxyethylborane as determined by $^{11}$Boron NMR.

Although the present invention has been described in detail in connection with the above examples, it is to be understood that such detail is solely for that purpose and that variations can be made therein by those skilled in the art without departing from the spirit and scope of the invention except as it may be limited by the following claims.

What is claimed is:

1. A process for the preparation of a diorganohaloborane compound of the structural formula of $R^2R^3BX$, comprising the step of reacting in a single reactor a first reactant R selected from the group consisting of an olefin and an alkyne, a second reactant $R^1$ selected from the group consisting of an olefin and an alkyne, diborane and a boron trihalide of the structural formula $BX_3$, wherein X is selected from the group consisting of a fluoro, a chloro, a bromo and an iodo group, the mole ratio of boron trihalide to diborane being in the range of approximately 1:1.5 to 1.5:1, wherein $R^2$ is an alkyl group corresponding to R in the case that R is an olefin, wherein $R^2$ is an alkenyl group corresponding to R in the case that R is an alkyne, wherein $R^3$ is an alkyl group corresponding to $R^1$ in the case that $R^1$ is an olefin, and wherein $R^3$ is an alkenyl group corresponding to $R^1$ in the case that $R^1$ is an alkyne.

2. The process of claim 1 where $R^2$ and $R^3$ are isopinocampheyl groups and X is selected from the group consisting of a chloro and a bromo group.

3. The process of claim 1 where $R^2$ and $R^3$ are cyclohexyl groups and X is selected from the group consisting of a chloro, a bromo and an iodo group.

4. The process of claim 1, wherein $R^2$ and $R^3$ are covalently linked to form a ring system.

5. The process of claim 1 wherein at least one of R and $R^1$ is an olefin of the general formula

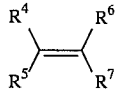

wherein each of $R^4$, $R^5$, $R^6$ and $R^7$ is selected from the group consisting of hydrogen, an aryl group, a branched alkyl group, an unbranched alkyl group and a cyclic group containing from one to ten carbon atoms.

6. The process of claim 5 wherein $R^4$ and $R^5$ are covalently linked by a $C_n$ chain wherein n=2–10.

7. The process of claim 5 or $R^4$ and $R^6$ are covalently linked by a $C_n$ chain wherein n=2–10.

8. The process of claim 1 wherein at least one of R and $R^1$ is an alkyne of the general formula:

wherein each of $R^8$ and $R^9$ are selected individually from the group consisting of hydrogen, an aryl group, a branched alkyl group, an unbranched alkyl group and a cyclic group containing from one to ten carbon atoms.

9. The process of claim 8 wherein $R^8$ and $R^9$ are covalently linked by a $C_n$ chain wherein n=8–15.

10. A process for the preparation of a organodihaloborane compound of the structural formula of $R^2BX_2$, comprising the step of reacting in a single reactor a first reactant R selected from the group consisting of an olefin and an alkyne, diborane and a boron trihalide of the structural formula $BX_3$, wherein X is selected from the group consisting of a fluoro, a chloro, a bromo and an iodo group, the ratio of boron trihalide to diborane being in the range of approximately 3:1 to 5:1, wherein $R^2$ is an alkyl group corresponding to R in the case that R is an olefin, and wherein $R^2$ is an alkenyl group corresponding to R in the case that R is an alkyne.

11. The process of claim 10 wherein R is an olefin of the general formula

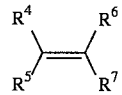

wherein each of $R^4$, $R^5$, $R^6$ and $R^7$ is selected from the group consisting of hydrogen, an aryl group, a branched alkyl group, an unbranched alkyl group and a cyclic group containing from one to ten carbon atoms.

12. The process of claim 11 wherein $R^4$ and $R^5$ are covalently linked by a $C_n$ chain wherein n=2–10.

13. The process of claim 11 wherein $R^4$ and $R^6$ are covalently linked by a $C_n$ chain wherein n=2–10.

14. The process of claim 10 wherein R is an alkyne of the general formula:

wherein each of $R^8$ and $R^9$ are selected individually from the group consisting of hydrogen, an aryl group, a branched alkyl group, an unbranched alkyl group and a cyclic group containing from one to ten carbon atoms.

15. The process of claim 14 wherein $R^8$ and $R^9$ are covalently linked by a $C_n$ chain wherein n=8–15.

16. A process for the preparation of a alkoxydiorganoborane compound of the structural formula of $R^2R^3BOR^{10}$, comprising the step of reacting in a single reactor a first reactant R selected from the group consisting of an olefin and an alkyne, a second reactant $R^1$ selected from the group consisting of an olefin and an alkyne, diborane and an alkyl borate of the structural formula $B(OR^{10})_3$, wherein $R^{10}$ is an alkyl group, the mole ratio of alkyl borate to diborane being in the range of approximately 1:1.5 to 1.5:1, wherein $R^2$ is an alkyl group corresponding to R in the case that R is an olefin, wherein $R^2$ is an alkenyl group corresponding to R in the case that R is an alkyne, wherein $R^3$ is an alkyl group corresponding to $R^1$ in the case that $R^1$ is an olefin, and wherein $R^3$ is an alkenyl group corresponding to $R^1$ in the case that $R^1$ is an alkyne.

17. A process for the preparation of a dialkoxyorganoborane compound of the structural formula of $R^2B(OR^{10})_2$, comprising the step of reacting in a single reactor a first reactant R selected from the group consisting of an olefin and an alkyne, diborane and an alkyl borate of the structural formula $B(OR^{10})_3$, wherein $R^{10}$ is an alkyl group, the mole ratio of alkyl borate to diborane being in the range of approximately 3:1 to 5:1, wherein $R^2$ is an alkyl group corresponding to R in the case that R is an olefin, wherein $R^2$ is an alkenyl group corresponding to R in the case that R is an alkyne.

* * * * *